US009622985B2

(12) United States Patent
Urushihara et al.

(10) Patent No.: US 9,622,985 B2
(45) Date of Patent: Apr. 18, 2017

(54) SUPPORT BODY FOR TRANSDERMAL PATCH OR TRANSDERMAL PREPARATION, AND TRANSDERMAL PATCH AND TRANSDERMAL PREPARATION USING SAME

(71) Applicant: NITTO DENKO CORPORATION, Osaka (JP)

(72) Inventors: Naoko Urushihara, Ibaraki (JP); Satoshi Ameyama, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 14/427,208

(22) PCT Filed: Sep. 20, 2013

(86) PCT No.: PCT/JP2013/075500
§ 371 (c)(1),
(2) Date: Mar. 10, 2015

(87) PCT Pub. No.: WO2014/046243
PCT Pub. Date: Mar. 27, 2014

(65) Prior Publication Data

US 2015/0238436 A1 Aug. 27, 2015

(30) Foreign Application Priority Data

Sep. 21, 2012 (JP) ................................ 2012-208538

(51) Int. Cl.
*A61K 9/70* (2006.01)
*A61M 35/00* (2006.01)

(52) U.S. Cl.
CPC .......... *A61K 9/7038* (2013.01); *A61K 9/7061* (2013.01); *A61M 35/00* (2013.01)

(58) Field of Classification Search
None
See application file for complete search history.

(56) References Cited

U.S. PATENT DOCUMENTS 4,898,805 A * 2/1990 Takada ................ H01L 21/4846 427/97.4
5,965,244 A * 10/1999 Tang ........................ B41M 5/52 347/105
2002/0058782 A1* 5/2002 Tomihisa .............. C08K 5/005 528/501
2003/0049420 A1* 3/2003 Inoue ..................... B41M 5/502 428/195.1
2007/0020417 A1* 1/2007 Murakami ............. B29C 61/06 428/35.7
2011/0117359 A1* 5/2011 de Santos Avila ... C09D 7/1225 428/325
2013/0052460 A1 2/2013 Iseki et al.

FOREIGN PATENT DOCUMENTS

EP 0501441 A2 * 9/1992
JP 63-185920 A 8/1988
JP H02-212419 A 8/1990
JP 3-35077 A 2/1991
JP 4-59722 A 2/1992
JP H04-59 A 2/1992
JP H05-84260 A 4/1993
JP H05-178742 A 7/1993
JP H05-310559 A 11/1993
JP H09-278650 A 10/1997
JP 11-130666 A 5/1999
JP 2000-327955 A 11/2000
JP 2004-143052 A 5/2004
JP 2007-269753 A 10/2007
KR 10-2008-0004726 A 1/2008
WO 2011/145620 A1 11/2011

OTHER PUBLICATIONS

International Search Report for PCT/JP2013/075500, mail date is Oct. 29, 2013.
Extended European Search Report issued in Patent Application No. 13840058.5, dated Apr. 14, 2016.
Office Action issued in Chinese Counterpart Patent Application No. 201380049046.6, dated Dec. 27, 2016.
English translation of Office Action issued in Chinese Counterpart Patent Application No. 201380049046.6, dated Dec. 27, 2016.

* cited by examiner

*Primary Examiner* — Robert A Wax
*Assistant Examiner* — Caralynne Helm
(74) *Attorney, Agent, or Firm* — Greenblum & Bernstein, P.L.C.

(57) ABSTRACT

The present invention provides a patch or patch preparation in which the anchoring property of a pressure-sensitive adhesive layer to a support is improved with no adverse effects on its pressure-sensitive adhesive properties such as adhesion, pressure-sensitive adhesiveness, and a cohesive strength. A support of the present invention is for a patch or patches preparation, and comprises a base material containing a plastic film and an undercoat agent layer laminated on the base material. The undercoat layer contains porous inorganic particles having an average particle diameter of from 1 μm to 15 μm. A patch and patch preparation of the present invention comprises the support and a pressure-sensitive adhesive layer placed on one surface of the support to be adjacent to the undercoat agent layer.

5 Claims, 2 Drawing Sheets

SUPPORT BODY FOR TRANSDERMAL PATCH OR TRANSDERMAL PREPARATION, AND TRANSDERMAL PATCH AND TRANSDERMAL PREPARATION USING SAME

TECHNICAL FIELD

The present invention relates to a patch and patch preparation excellent in anchoring properties.

BACKGROUND ART

In recent years, various kinds of, for example, tapes each using a pressure-sensitive adhesive have been developed as patch preparations for administering a drug into a living organism through the surface of a skin. A drug concentration in the pressure-sensitive adhesive needs to be increased to some extent in order that the drug may be effectively released from the patch preparation to the surface of the skin and may be absorbed in the skin. However, increasing the drug concentration causes the following problem. The drug is brought into a supersaturated state or a crystalline state in the pressure-sensitive adhesive, the anchoring property of the pressure-sensitive adhesive to a support reduces, and hence the pressure-sensitive adhesive remains on the surface of the skin upon removal of the patch preparation from the skin.

To solve such problem, by forming a pressure-sensitive adhesive layer on a support having laminated thereon a nonwoven fabric, a woven fabric, or the like, there has been proposed a patch in which the anchoring property of a pressure-sensitive adhesive to a support is improved and hence the adhesive residue of the pressure-sensitive adhesive is prevented (Patent Literature 1). The patch causes no problem when the pressure-sensitive adhesive layer has an enough thickness to cover the unevenness of the nonwoven fabric or the woven fabric. However, when the thickness of the pressure-sensitive adhesive layer containing a drug is reduced in consideration of the utilization ratio of the drug, the following problem arises. The pressure-sensitive adhesive layer cannot completely cover the unevenness of the nonwoven fabric or the woven fabric, and hence its adhesion to the skin reduces, or conversely, an adhesive residue on the skin is liable to occur.

Patent Literature 2 proposes a technology involving using an isocyanate-based compound as an undercoat agent for the surface of a support to improve the anchoring property of a pressure-sensitive adhesive layer to the support. However, the isocyanate-based compound has so short a pot life that means for, for example, blocking moisture or controlling a reaction temperature to a low temperature is needed. Accordingly, an operation becomes extremely complicated. Further, the isocyanate-based compound has high reactivity, and hence may cause a cross-linking reaction or the like with a pressure-sensitive adhesive to change its pressure-sensitive adhesive properties or may cause a decomposition reaction with a drug depending on the kind of the pressure-sensitive adhesive or the drug. Accordingly, sufficient care needs to be taken upon use of the compound.

Patent Literature 3 proposes that the anchoring property of a pressure-sensitive adhesive layer to a support be improved by: applying a primer composition containing fine particles having an average particle diameter of 100 nm or less onto the surface of the support; and forming the pressure-sensitive adhesive layer on the applied composition. However, the primer composition in the literature is poor in handleability and involves a problem in terms of its dispersibility in a liquid, and hence an additional improvement in anchoring property of a patch preparation has been required.

CITATION LIST

Patent Literature

[PTL 1] JP 02-212419 A
[PTL 2] JP 05-310559 A
[PTL 3] JP 2000-327955 A

SUMMARY OF INVENTION

Technical Problem

The present invention has been made to solve the problems, and an object of the present invention is to provide a patch or patch preparation in which the anchoring property of a pressure-sensitive adhesive layer to a support is improved with no adverse effects on its pressure-sensitive adhesive properties such as adhesion, pressure-sensitive adhesiveness, and a cohesive strength.

Means for Solving the Problems

According to the present invention, a support body for a patch or patch preparation is provided. A support for a patch or patch preparation comprises a base material containing a plastic film; and an undercoat agent layer laminated on the base material. The undercoat layer contains porous inorganic particles having an average particle diameter of from 1 μm to 15 μm.

In a preferred embodiment, the porous inorganic particles have a pore volume of from 0.5 ml/g to 2.5 ml/g.

In a preferred embodiment, the undercoat agent layer has a basis weight of from 0.1 $g/m^2$ to 10 $g/m^2$.

In a preferred embodiment, the porous inorganic particles comprise porous silica particles.

In a preferred embodiment, the base material contains a polyolefin-based resin film.

In a preferred embodiment, the undercoat agent layer further contains a binder resin.

According to another aspect of the present invention, a patch is provided. The patch comprises the above support and a pressure-sensitive adhesive layer placed on one surface of the support to be adjacent to the undercoat agent layer.

Furthermore, according to another aspect of the present invention a patch preparation is provided. The patch preparation comprises the above patch. The pressure-sensitive adhesive layer further contains a drug.

Advantageous Effects of Invention

According to one embodiment of the present invention, the problems are solved by providing the undercoat agent layer containing the porous inorganic particles having a predetermined average particle diameter on the surface on the side of the support where the pressure-sensitive adhesive layer is provided to form unevenness, and the anchoring property of the pressure-sensitive adhesive layer to the support can be improved.

DESCRIPTION OF EMBODIMENTS

[A. Support]

Figure 1:
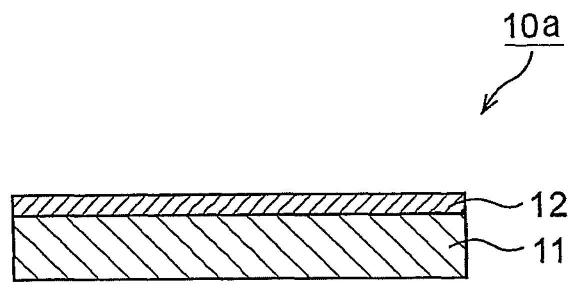
FIG. 1 is a schematic sectional view of a support according to a preferred embodiment of the present invention.

FIG. 1 is a schematic sectional view of a support according to a preferred embodiment of the present invention. A support 10*a* includes a base material 11 and an undercoat agent layer 12 laminated on the base material (one surface). The undercoat agent layer 12 contains porous inorganic particles having an average particle diameter of from 1 μm to 15 μmin and preferably having a pore volume of from 0.5 ml/g to 2.5 ml/g.

Figure 2:
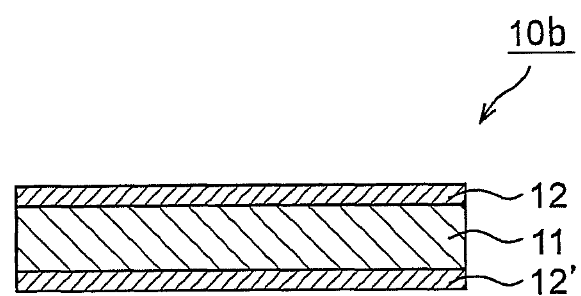
FIG. 2 is a schematic sectional view of a support according to another preferred embodiment of the present invention.

FIG. 2 is a schematic sectional view of a support according to another preferred embodiment of the present invention. A support 10*b* includes the base material 11, and undercoat agent layers 12 and 12' laminated on both surfaces of the base material. The undercoat agent layer 12' contains porous inorganic particles having an average particle diameter of from 1 μm to 15 μm and preferably having a pore volume of from 0.5 ml/g to 2.5 ml/g.

The supports 10*a* and 10*b* can each be suitably used as a support for a patch or patch preparation to be described later.

[A-1. Base Material]

The base material 11 contains a plastic film. Specific examples of the base material include: various plastic films including polyester-based resin films such as a polyvinyl chloride-based resin film and polyethylene terephthalate, polyolefin-based resin films such as polyethylene, polypropylene, an ethylene-vinyl acetate copolymer, and an ethylene-vinyl alcohol copolymer, and polyurethane-based resin films; and laminates obtained by laminating nonwoven fabrics on the plastic films. The base material preferably contains any one of the polyolefin-based resin films because an undercoat agent containing a solvent can be applied onto each of the films, and the films are each excellent in flexibility and skin followability, and the base material more preferably contains an ethylene-vinyl alcohol copolymer resin film out of the films in terms of skin followability.

The plastic film has a thickness of, for example, from 1.0 μm to 80 μm, preferably from 2.0 μm to 40 μm, more preferably from 2.0 μm to 30 μm.

In the present invention, it is advantageous to use a support on which no nonwoven fabric has been laminated. The lamination of a nonwoven fabric may reduce the handleability of the support because the lamination increases the thickness of the support to make the support bulky. In the invention of the present application, the anchoring property of a pressure-sensitive adhesive layer can be improved by providing the undercoat agent layer to be described later while the need for the lamination of the nonwoven fabric is eliminated.

The thickness of the base material 11 can be appropriately set depending on purposes and the like. The thickness is, for example, from 1.0 μm to 100 μm, preferably from 2.0 μm to 60 μm, more preferably from 2.0 μm to 40 μm, still more preferably from 2.0 μm to 30 μm.

[A-2. Undercoat Agent Layer]

The undercoat agent layer 12 or 12' contains the porous inorganic particles. The undercoat agent layer preferably further contains a binder resin for adhering the porous inorganic particles to the base material. The undercoat agent layer can be typically formed by: applying an undercoat agent containing the porous inorganic particles, the binder resin, and a solvent onto the surface of the base material; and solidifying and/or curing the agent.

The average particle diameter of the porous inorganic particles in the undercoat agent layer 12 or 12' is from 1 μm to 15 μm, preferably from 1 μm to 10 μm, more preferably from 1.5 μm to 9 μm, still more preferably from 3.2 μm to 9.0 μm. When the average particle diameter is less than 1 μm, the following problem arises: the pore volume in the particles reduces and hence an anchoring force-improving effect becomes insufficient. On the other hand, when the average particle diameter exceeds 15 μm, such a problem as described below arises: the particles are liable to sediment in the undercoat agent or the anchoring force-improving effect becomes insufficient. Here, the average particle diameter of the porous inorganic particles is a value (median diameter in terms of a volume) obtained by measurement in which a secondary particle is also regarded as one particle, and a primary particle and the secondary particle are not distinguished from each other. In addition, the shape of each of the porous inorganic particles may not be a true spherical shape as long as the particles have an average particle diameter of from 1 μm to 15 μm.

In the present invention, the average particle diameter of the porous inorganic particles in the undercoat agent layer can be typically equated with the average particle diameter of the porous inorganic particles in the undercoat agent, and hence the average particle diameter (in terms of a volume) of the porous inorganic particles in the undercoat agent measured by a laser diffraction/scattering-type particle size distribution-measuring method can be defined as the average particle diameter of the porous inorganic particles in the undercoat agent layer. In addition, the actual measurement of the average particle diameter of the porous inorganic particles in the undercoat agent layer can be performed with, for example, a three-dimensional measuring X-ray CT apparatus as described below. That is, transmission image data is acquired by irradiating the exposed surface of the undercoat agent layer with an X-ray while rotating a sample in the angle range of from 0° to 180°. The particle diameters of any 100 particles that can be observed in any region in a three-dimensional stereoscopic image thus obtained (e.g., a 5-mm$^2$ area holding a sufficient resolution) are measured, and the average particle diameter is calculated from their particle size distribution. It should be noted that in the case of particles that are not spherical, the particle diameters of spherical particles having the same volumes as those of the particles are calculated. The foregoing measurement is performed three times and the arithmetic average median diameter of the three measured results is defined as the average particle diameter.

The surfaces of the porous inorganic particles each preferably have high adsorptive activity. The pore volume of the porous inorganic particles is preferably from 0.5 ml/g to 2.5 ml/g, more preferably from 0.7 ml/g to 2.0 ml/g, still more preferably from 1.4 ml/g to 1.7 ml/g. When the pore volume of the particles is less than 0.5 ml/g, unevenness on their surfaces is small and hence the anchoring force-improving effect becomes insufficient in some cases. On the other hand, when the pore volume of the particles exceeds 2.5 ml/g, the particles are liable to break and hence it becomes difficult to maintain the shapes of the particles in some cases. The pore volume can be measured by a pore distribution-measuring method based on a nitrogen adsorption method.

Examples of the porous inorganic particles include porous silica particles, porous alumina particles, and porous titania particles. Of those, porous silica particles can be preferably used because the particles hardly break even during a production process or in a dispersion liquid. It should be noted that only one kind of the porous inorganic particles may be used, or two or more kinds thereof may be used in combination.

The porous silica particles can be roughly classified into dry silica particles and wet silica particles depending on their production method. The dry silica particles are produced by burning a silane-based gas such as silicon tetrachloride in oxyhydrogen flames (dry method). The dry silica particles have the following characteristics: their particle diameters are small and their specific surface area is small. In general, the particles loosely adhere to each other to exist as an aggregated particle or an agglomerated particle. On the other hand, the wet silica particles are obtained by precipitation through a reaction between sodium silicate and a mineral acid (wet method). The wet silica particles have the following advantage: the particles have higher liquid-absorbing properties than those of the dry silica particles and hence the selection of the binder resin to be described later widens. In the present invention, the wet silica particles are more preferred because the anchoring property-improving effect is strongly exhibited when inorganic particles that are additionally porous and excellent in liquid-absorbing properties are used.

The pH of the porous silica particles is not particularly limited and can be any appropriate pH. The pH is preferably a circumneutral value (e.g., pH=6.0 to 8.0) in consideration of influences on a pressure-sensitive adhesive and any appropriate additive or drug to be incorporated into the pressure-sensitive adhesive layer.

The affinities of the surfaces of the porous silica particles for the binder resin and solvent to be described later may be improved as required by treating the surfaces with organic matter. It is desired that the surface characteristics of the porous silica particles be appropriately selected depending on, for example, the kind of the binder resin.

Only one kind of the porous silica particles may be used, or two or more kinds thereof may be used in combination. Commercially available porous silica particles can also be used. The commercially available porous silica particles are specifically exemplified by trade names “SYLOID 72FP” and “SYLOID 244FP” (manufactured by W. R. Grace), trade names “SYLYSIA” and “SYLOSPHERE” (manufactured by FUJI SILYSIA CHEMICAL LTD.), trade names “NIPGEL” and “Nipsil” (manufactured by Tosoh Silica Corporation), a trade name “MIZUKASIL” (manufactured by Mizusawa Industrial Chemicals, Ltd.), “SILCRON” (manufactured by SCM GLIDCO ORGANICS CORPORATION), and a trade name “GASIL” (manufactured by Crosfield).

Any appropriate resin can be used as the binder resin as long as the resin can adhere the porous inorganic particles to the base material. For example, a binder resin that has been used conventionally can be used. Examples of such binder resin include a urethane-based resin, an ethyleneimine-based resin, an aminoethyl-based resin, and a polyester-based resin. It should be noted that various binders containing those binder resins, and compounded with a solvent or a dispersion medium and any other additive or the like are commercially available, and hence these commercial products can also be used in the present invention. Examples of the binders include: binders each using an aqueous solvent or dispersion medium such as water or an alcohol; and binders each using an organic solvent-based solvent or dispersion medium such as benzene or ethyl acetate. More specific examples thereof include: a solvent-based urethane binder typified by a trade name “MITEC NY218A” (manufactured by Mitsubishi Chemical Corporation) or a trade name “TAKENATE B-800” (manufactured by Takeda Pharmaceutical Company Limited); an aqueous urethane binder typified by a trade name “TAKELAC W-710” (manufactured by Takeda Pharmaceutical Company Limited); an ethyleneimine binder typified by a trade name “EPOMIN SP300” (manufactured by NIPPON SHOKUBAI CO., LTD.); a solvent-based aminoethyl binder typified by a trade name “POLYMENT NK-200” (manufactured by NIPPON SHOKUBAI CO., LTD.); an aqueous aminoethyl binder typified by a trade name “POLYMENT SK-1000” (manufactured by NIPPON SHOKUBAI CO., LTD.); and a polyester-based binder typified by a trade name “VYLON 200” (manufactured by Toyobo Co., Ltd.).

In another embodiment, a resin having no adhesion can be used as the binder resin. Specifically, the resin having no adhesion is dissolved in a solvent, an undercoat agent is prepared by dispersing the porous inorganic particles in the solution, and the undercoat agent is applied onto the surface of the base material, followed by curing through drying and/or photoirradiation. Thus, the resin having no adhesion can function as a binder.

A resin excellent in compatibility with the base material and excellent in property by which the porous inorganic particles are fixed can be preferably used as the resin having no adhesion. This is because the porous inorganic particles can be satisfactorily fixed to the surface of the base material without the occurrence of any break between the undercoat agent layer and the base material. In addition, a resin that dissolves in a solvent and is dried to solidify is preferred from a production viewpoint. Examples of such resin include a PET resin, an ethylene-vinyl alcohol copolymer resin, and a polyethylene resin. Of those, the same resin as that used in the base material can be preferably used. The term “same resin” as used herein means that when the resins are polymers, the resins have a common monomer species, preferably the same monomer species. Resins having different molecular weights are the same resin as long as the resins have a common monomer species.

The undercoat agent can be prepared by dispersing or dissolving the porous inorganic particles and the binder resin in any appropriate solvent. A solvent excellent in property by which the porous inorganic particles are dispersed and excellent in miscibility with the binder resin can be appropriately selected as the solvent. Specific examples of the solvent include water, methanol, ethanol, 1-propanol, 2-propanol, ethyl acetate, methyl ethyl ketone, and toluene. The solvents may be used alone or in combination.

The compounding amount of the porous inorganic particles in the undercoat agent is preferably from 0.1 part by weight to 200 parts by weight, more preferably from 1 part by weight to 200 parts by weight, still more preferably from 20 parts by weight to 180 parts by weight with respect to 100 parts by weight of the binder resin. When the compounding amount of the porous inorganic particles is less than 0.1 part by weight, the porous inorganic particles are liable to embed in the binder resin and hence the surface of the support cannot be provided with sufficient unevenness in some cases. In addition, when the compounding amount exceeds 200 parts by weight, it may become difficult to uniformly disperse the porous inorganic particles in the undercoat agent. The solid content concentration of the undercoat agent can be set to any appropriate value from the viewpoint of, for example, workability.

The basis weight (weight per unit area) of the undercoat agent layer 12 or 12' can be appropriately set depending on, for example, the kind of the base material or the pressure-sensitive adhesive layer, applications, and purposes. The basis weight is preferably from 0.1 $g/m^2$ to 10 $g/m^2$, more preferably from 0.1 $g/m^2$ to 8 $g/m^2$, still more preferably from 0.2 $g/m^2$ to 5 $g/m^2$. With such basis weight, a uniform undercoat agent layer is obtained and the surface of the support can be provided with sufficient unevenness. The basis weight can be adjusted to a desired value by appropriately setting, for example, the solid content concentration and application amount of the undercoat agent. In particular, when the undercoat agent contains a water dispersion-type binder resin, the application amount in which a uniform coating film (i.e., undercoat agent layer) is obtained is preferably selected depending on the average particle diameter of the porous inorganic particles.

[B. Patch]

Figure 3:
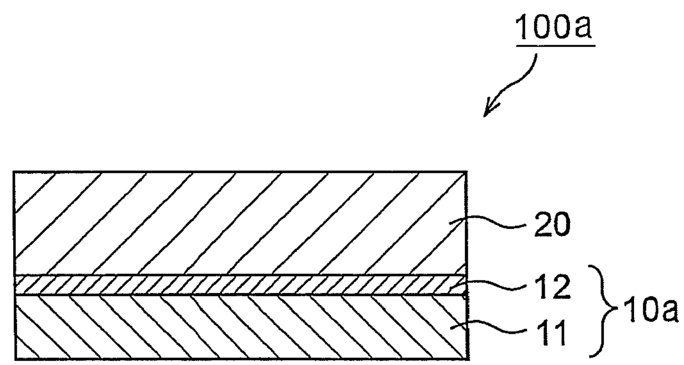
FIG. 3 is a schematic sectional view of a patch according to a preferred embodiment of the present invention.
Figure 4:
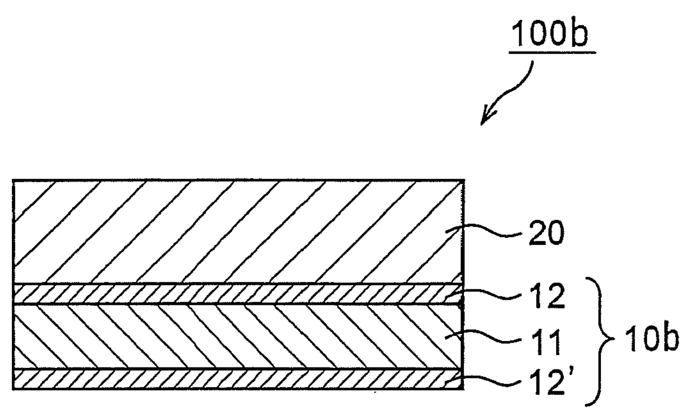
FIG. 4 is a schematic sectional view of a patch according to another preferred embodiment of the present invention.

FIG. 3 is a schematic sectional view of a patch according to a preferred embodiment of the present invention. A patch 100*a* includes the support 10*a* and a pressure-sensitive adhesive layer 20 placed on one surface of the support 10*a* to be adjacent to the undercoat agent layer 12. In addition, FIG. 4 is a schematic sectional view of a patch according to another preferred embodiment of the present invention. A patch 100*b* includes the support 10*b* and the pressure-sensitive adhesive layer 20 placed on one surface of the support 10*b* to be adjacent to the undercoat agent layer 12. According to the patch 100*b* using the support 10*b* including the undercoat agent layer 12', the following effects can be obtained: an external appearance at the time of its attachment is excellent and the strength of the support 10*b* is increased to prevent, for example, the occurrence of a wrinkle. In practical use, a release liner is provided on the surface of the pressure-sensitive adhesive layer 20 of the patch 100*a* or 100*b* (not shown).

[B-1. Support]

The support described in the section A is used as each of the support 10*a* and 10*b*.

[B-2. Pressure-Sensitive Adhesive Layer]

The pressure-sensitive adhesive layer 20 contains a pressure-sensitive adhesive. Any appropriate pressure-sensitive adhesive can be used as the pressure-sensitive adhesive depending on, for example, the kind of the base material or the undercoat agent and purposes. Examples thereof include an acrylic pressure-sensitive adhesive, a natural rubber-based pressure-sensitive adhesive, a synthetic rubber-based pressure-sensitive adhesive, and a silicone-based pressure-sensitive adhesive. One kind of those pressure-sensitive adhesives may be used alone, or two or more kinds thereof may be used in combination. Although any one of the pressure-sensitive adhesives can be used in the present invention, the synthetic rubber-based pressure-sensitive adhesive and/or the acrylic pressure-sensitive adhesive are each/is preferably used. The acrylic pressure-sensitive adhesive is particularly advantageous because according to the acrylic pressure-sensitive adhesive, the anchoring force-improving effect is exhibited without being influenced by a functional group in the pressure-sensitive adhesive.

The acrylic pressure-sensitive adhesive means an adherent composition that contains an acrylic polymer as an adherent polymer having pressure-sensitive adhesiveness at normal temperature and is compounded with a tackifier as required. The acrylic polymer is a polymer obtained by polymerizing monomer components including an acrylic monomer such as an alkyl(meth)acrylate or (meth)acrylic acid as a main component. Here, the main component means a monomer whose content is 50 wt % or more based on the total weight of all the monomers constituting the polymer.

The natural or synthetic rubber-based pressure-sensitive adhesive means an adherent composition obtained by compounding an elastomer such as natural rubber, polyisoprene, a styrene-isoprene-styrene block copolymer (SIS), a styrene-butadiene-styrene block copolymer (SBS), or polyisobutylene with a tackifier such as a rosin-based, terpene-based, or petroleum-based tackifier as required. The tackifier is typically compounded at a content of from 10 to 50 wt % based on the total weight of the pressure-sensitive adhesive.

The silicone-based pressure-sensitive adhesive means an adherent composition obtained by compounding a silicone rubber with a tackifier such as a silicone resin as required. The tackifier is typically compounded at a content of from 10 to 50 wt % based on the total weight of the pressure-sensitive adhesive.

A hydrophobic pressure-sensitive adhesive layer is preferred and a nonaqueous pressure-sensitive adhesive layer is more preferred from the viewpoint of skin adhesion. The term "nonaqueous pressure-sensitive adhesive layer" as used herein is not necessarily limited to a layer completely free of moisture and comprehends a layer substantially free of water, i.e., a layer containing a slight amount of moisture derived from air humidity, the skin, or the like. The expression "slight amount of moisture" as used herein refers to a moisture content of a laminate of the support and the pressure-sensitive adhesive layer of preferably 5 wt % or less, more preferably 2 wt % or less, most preferably 1 wt % or less.

The moisture content of the laminate of the support and the pressure-sensitive adhesive layer means the weight ratio of water in the laminate of the support and the pressure-sensitive adhesive layer from which a release liner, if present, has been peeled (the weight percentage of water with respect to the total weight of the laminate of the support and the pressure-sensitive adhesive layer), the weight ratio being measured by a Karl-Fischer coulometric titration method, and is specifically as described below. That is, a test piece is produced by punching a sample having the release liner, if present, into a predetermined size under an environment having a temperature and a relative humidity controlled to 23±2° C. and 40±5% RH, respectively. After that, the release liner, if present, is removed from the test piece and the test piece is loaded into a moisture vaporizer. The test piece is heated at 140° C. in the moisture vaporizer, moisture produced by the heating is introduced into a titration flask by using nitrogen as a carrier, and the moisture content (wt %) of the sample is measured by the Karl-Fischer coulometric titration method.

The pressure-sensitive adhesive layer 20 can contain any appropriate additive as required. Examples of the additive include: softening agents such as an ester of a monobasic acid or a polybasic acid and a branched alcohol, and/or an ester of an unsaturated fatty acid or branched acid and an alcohol that is tetrahydric or less; cross-linking agents such as isocyanate-, epoxy-, and metal ion-based cross-linking agents; and organic liquid components such as a fatty acid alkyl ester and a fatty acid triglyceride. One kind of those additives can be used alone, or two or more kinds thereof can be used in combination. The content of any such additive in the pressure-sensitive adhesive layer can be appropriately set depending on purposes and the like.

The content of the pressure-sensitive adhesive in the pressure-sensitive adhesive layer 20 is preferably from 30 wt % to 100 wt %, more preferably from 40 wt % to 100 wt % based on the total weight of the pressure-sensitive adhesive layer. When the content of the pressure-sensitive adhesive is less than 30 wt %, the internal cohesive strength of the pressure-sensitive adhesive layer may reduce.

The thickness of the pressure-sensitive adhesive layer 20 is preferably from 10 to 300 μm, more preferably from 15 to 200 μm, most preferably from 20 to 100 μm from the viewpoint of the skin adhesion.

[B-3. Release Liner]

The release liner is not particularly limited. Specific examples of the release liner include glassine paper, polyethylene, polypropylene, polyester, polyethylene terephthalate, polystyrene, an aluminum film, a polyethylene foam film, and a polypropylene foam film, and a laminated product thereof, a siliconized product thereof, and an embossed product thereof. A release liner made of a polyester (especially polyethylene terephthalate) resin is preferred in terms of barrier property, a price, and the ease with which a material for the liner is selected. The surface on the pressure-sensitive adhesive layer side of the release liner may be subjected to surface release treatment in order that the release liner can be peeled from the pressure-sensitive adhesive layer with additional ease.

The release liner preferably has a uniform thickness in consideration of the ease of processing and processing accuracy. The thickness of the release liner is preferably from 25 μm to 200 μm, more preferably from 50 μm to 150 μm from the viewpoints of, for example, the ease with which the patch is produced, a cost for the release liner, and the portability and operability of the patch.

[C. Patch Preparation]

A patch preparation of the present invention includes the patch in which the pressure-sensitive adhesive layer further contains a drug. The drug is not particularly limited. A drug which can be administered to mammals such as humans through their skin, that is to say, a drug capable of transdermal absorption is preferred. Specific examples of such drug include general anesthetics, hypnotics and sedatives, antiepileptics, antipyretic analgesics, anti-vertigenous drugs, psychoneurotic agents, central nervous system agents, antidementia drugs, local anesthetics, skeletal muscle relaxants, autonomic nervous system agents, spasmolytics, antiparkinson agents, antihistamines, cardiac stimulants, antiarrhythmic agents, diuretics, hypotensive agents, vasoconstrictors, coronary vasodilators, peripheral vasodilators, antiarteriosclerosis agents, cardiovascular system preparations, anapnoics, antitussives and expectorants, hormone preparations, dermatics for purulence, analgesics, anti-itchings, astrigents and anti-inflammatory agents, anti-dermoinfectives, hemostatics, gout suppressants, antidiabetic agents, antineoplastics, antibiotics, chemotherapeutics, narcotics, and smoking-cessation aids.

The drug can be present in the pressure-sensitive adhesive layer in an amount enough to provide a desired result, e.g., a desired therapeutic result in the therapy of a disease, a state, or a disorder (that is, an effective dose). The term "effective dose of the drug" means, for example, such a sufficient amount of the drug that the drug is nontoxic but provides a selected effect over a specific time period. Such amount can be easily determined by a person skilled in the art.

The content of the drug in the pressure-sensitive adhesive layer is not particularly limited as long as its effect as a drug for transdermal absorption is satisfied and the adhesion characteristic of the pressure-sensitive adhesive is not impaired. Specifically, the content of the drug is preferably from 0.1 wt % to 60 wt %, more preferably from 0.5 wt % to 40 wt % based on the total weight of the pressure-sensitive adhesive layer. When the content of the drug is less than 0.1 wt %, its therapeutic effect may be insufficient. When the content of the drug is more than 60 wt %, the contents of the pressure-sensitive adhesive and any other additive constituting the pressure-sensitive adhesive layer reduce, and hence sufficient skin adhesion may not be obtained. In addition, such content may be economically disadvantageous.

[D. Method of Producing Patch or Patch Preparation]

The patch or patch preparation of the present invention can be produced by any appropriate method. Examples thereof include the following methods. First, a support is obtained by: applying an undercoat agent in a thin layer shape to one surface, or each of both surfaces, of a base material; drying and removing a solvent after the application; and curing the remainder with UV light as required. Here, the surface of the base material may be subjected to any appropriate surface treatment such as corona treatment in advance from the viewpoint of improving adhesiveness between the base material and the undercoat agent layer. Applying means is not particularly limited, and any appropriate means such as a kiss coater, a gravure coater, a bar coater, or a spray coater can be applied. Next, a laminated sheet is obtained by: preparing a release liner; laminating a pressure-sensitive adhesive layer on one surface of the release liner; and laminating the support on the pressure-sensitive adhesive layer. Alternatively, the laminated sheet is obtained by: laminating the pressure-sensitive adhesive layer on the undercoat agent layer surface of the support; and laminating the release liner on the pressure-sensitive adhesive layer. An approach to laminating the support and the pressure-sensitive adhesive layer is not particularly limited. Specific examples thereof include application, bonding, fusion, and welding. Preferably adopted is a method involving: preparing a composition for forming a pressure-sensitive adhesive layer containing a pressure-sensitive adhesive and an organic solvent, and as required, a drug or the like; applying the composition onto the release liner or the support; and drying and removing the organic solvent after the application. The patch or the patch preparation is obtained by cutting the resultant laminated sheet into a predetermined shape. The patch or the patch preparation can be packaged with any appropriate packaging container as desired. Bags and the like produced from a resin film, a metal foil, and a laminated film thereof are each typically used as the packaging container.

EXAMPLES

Hereinafter, Examples of the present invention are described. However, the present invention is not limited thereto.

<<Measurement of Average Particle Diameter>>

The average diameter of particles in an undercoat agent in terms of a volume was measured with a laser diffraction-type particle diameter distribution-measuring apparatus (manufactured by SHIMADZU CORPORATION).

<<Measurement of Pore Volume>>

A pore volume was measured with a pore distribution-measuring apparatus based on a gas adsorption method by a nitrogen adsorption method.

Example 1

(1) 43 Parts by weight of 2-ethylhexyl acrylate, 43 parts by weight of butyl acrylate, and 14 parts by weight of diacetone acrylamide as monomers were Loaded into a reaction vessel provided with a cooling tube, a nitrogen gas-introducing tube, a temperature gauge, a dropping funnel, and a stirring machine, and were stirred in ethyl acetate. 0.2 Part by weight of 2,2'-azobisisobutyronitrile as a polymerization initiator was added to the monomers. Such control that the temperature of the contents was kept at 40° C. was performed by, for example, the adjustment of a stirring speed, the adjustment of an external bath temperature, and the dropping of ethyl acetate as a diluent solvent, followed by polymerization in a stream of a nitrogen gas for 90 minutes. Next, the temperature was held at 60° C. for 6 hours and held at 80° C. for 18 hours. A solution of an acrylic copolymer (A) was obtained by the solution polymerization.

(2) The acrylic polymer solution (A) was diluted with ethyl acetate to provide a composition for forming a pressure-sensitive adhesive layer containing an acrylic pressure-sensitive adhesive. The composition was applied onto a release liner (polyester film whose surface had been subjected to release treatment) so that its thickness after drying became 40 μm, and the applied composition was dried to form a pressure-sensitive adhesive layer.

Meanwhile, an ethylene-vinyl alcohol copolymer resin (EVOH resin) (product name "E105", manufactured by KURARAY CO., LTD.) and silica particles (trade name "SYLOID 72FP", manufactured by W.R. Grace) were dissolved and dispersed at a compounding ratio (on a weight basis) of 1:1 in a mixed solvent of n-propanol and water (n-propanol/water=8/2 (on a volume basis)) to provide an undercoat agent. The resultant undercoat agent was applied onto one surface of a base material (20-μm thick EVOH film (product name "EF-E", manufactured by KURARAY CO., LTD.)) so that the basis weight of a coating film (undercoat agent layer) after drying became 0.6 g/m$^2$, and the applied agent was dried to form an undercoat agent layer. Thus, a support was obtained. The pressure-sensitive adhesive layer was transferred onto the undercoat agent layer surface of the resultant support to provide a patch 1.

Examples 2 to 10

Patches 2 to 10 were obtained in the same manner as in Example 1 except that different kinds of silica particles were used.

Comparative Example 1

A patch C1 was obtained in the same manner as in Example 1 except that a different kind of silica particles was used.

Comparative Example 2

A patch C2 was obtained in the same manner as in Example 1 except that an undercoat agent was prepared without the addition of the silica particles.

Comparative Example 3

10 Parts by weight of silica particles (trade name "SYLOID 72FP", manufactured by W.R. Grace) with respect to 90 parts by weight of the solid content of the composition for forming a pressure-sensitive adhesive layer containing the acrylic pressure-sensitive adhesive used in Example 1 were added and mixed in the composition to provide a composition for forming a pressure-sensitive adhesive layer containing the silica particles. A pressure-sensitive adhesive layer was formed by using the composition and an undercoat agent was prepared without the addition of the silica particles. A patch C3 was obtained in the same manner as in Example 1 except the foregoing.

Comparative Example 4

A patch C4 was obtained in the same manner as in Example 1 except that: silica particles (trade name "AEROSIL 200", manufactured by NIPPON AEROSIL CO., LTD.) were added at a compounding ratio of 5 parts by weight with respect to 100 parts by weight of the EVOH resin to prepare an undercoat agent; and the basis weight of an undercoat agent layer was set to 0.3 g/m$^2$.

Comparative Example 5

A patch C5 was obtained in the same manner as in Example 1 except that: sodium chloride (manufactured by Wako Pure Chemical Industries, Ltd.) (its particle diameter was adjusted after its acquisition) was used instead of the silica particles; and the basis weight of an undercoat agent layer was set to 0.3 g/m$^2$.

Each of the patches 1 to 10 and C1 to C5 was attached to a SUS plate covered with a Celgard (manufactured by Hoechst AG), and was then peeled with a Tensilon tensile tester in a 180° direction at a rate of 100 mm/min. A failure mode at the time of the peeling was evaluated by the following criteria. Table 1 shows the results.

[Evaluation Criteria]

○: The patch underwent no anchoring failure.

Δ: The patch partially underwent anchoring failure.

x: The patch underwent anchoring failure.

TABLE 1

| | Silica | | | | |
|---|---|---|---|---|---|
| | Average particle diameter (μm) | Pore volume (ml/g) | Shape | Trade name | Failure mode |
| Example 1 | 6.0 | 1.2 | Amorphous | SYLOID 72FP*1 | ○ |
| Example 2 | 3.2 | 1.5 | Amorphous | SYLOID 244FP*1 | ○ |
| Example 3 | 3.9 | 1.6 | Amorphous | SYLYSIA 350*2 | ○ |
| Example 4 | 9.0 | 1.6 | Amorphous | SYLYSIA 380*2 | ○ |
| Example 5 | 3.9 | 0.8 | Amorphous | SYLYSIA 550*2 | ○ |
| Example 6 | 4.5 | 1.5 | Spherical (sphericity: 0.9) | SYLOSPHERE C1504*2 | ○ |
| Example 7 | 1.8 | 2.0 | Amorphous | NIPGEL AZ-204*3 | ○ |
| Example 8 | 6.0 | 0.4 | Amorphous | SYLOID 63FP*1 | Δ |
| Example 9 | 4.0 | 0.4 | Amorphous | SYLYSIA 730*2 | Δ |
| Example 10 | 11.3 | 0.4 | Amorphous | SYLYSIA 780*2 | Δ |

TABLE 1-continued

| | Silica | | | | |
|---|---|---|---|---|---|
| | Average particle diameter (μm) | Pore volume (ml/g) | Shape | Trade name | Failure mode |
| Comparative Example 1 | 55.0 | 0.8 | Amorphous | COSMESILICA BQ60*2 | x |
| Comparative Example 2 | | | | | x |
| Comparative Example 3*5 | 6.0 | 1.2 | Amorphous | SYLOID 72FP*1 | x |
| Comparative Example 4 | 0.012 | No pore | Amorphous | AEROSIL 200*4 | x |
| Comparative Example 5 | 7 | No pore | Amorphous | Sodium chloride | x |

*1Manufactured by W.R. Grace
*2Manufactured by FUJI SILYSIA CHEMICAL LTD.
*3Manufactured by TOSOH SILICA CORPORATION
*4Manufactured by NIPPON AEROSIL CO., LTD.
*5Silica particles were added to a pressure-sensitive adhesive layer.

Comparison between each of the patches 1 to 10 and the patch C2 shows that an anchoring force is improved by providing an undercoat agent layer containing silica particles on the surface of a support in contact with a pressure-sensitive adhesive layer. In addition, comparison between each of the patches 1 to 10 and the patch C1 shows that silica particles having an average particle diameter of from 1 μm to 15 μm exhibit an anchoring force-improving effect. Comparison between each of the patches 1 to 7 and each of the patches 8 to 10 shows that silica particles having a pore volume of 0.5 ml/g or more exhibit an excellent anchoring force-improving effect. In addition, the anchoring forces of the patches C3 to C5 were insufficient.

Example 11

10 Parts by weight of isopropyl myristate as an organic liquid component with respect to 90 parts by weight of the solid content of a commercial acrylic pressure-sensitive adhesive (trade name "Duro-Tak 87-9301", manufactured by National Starch and Chemical Company) were added to the pressure-sensitive adhesive. The contents were stirred in an ethyl acetate solution to provide a composition for forming a pressure-sensitive adhesive layer.

A patch 11 was obtained in the same manner as in Example 3 except that the resultant composition for forming a pressure-sensitive adhesive layer was applied onto a release liner (polyester film whose surface had been subjected to release treatment) so that its thickness after drying became 40 μm, and the applied composition was dried to form a pressure-sensitive adhesive layer.

Example 12

An acrylic copolymer was obtained by copolymerizing 72 parts by weight of 2-ethylhexyl acrylate, 25 parts by weight of N-vinyl-2-pyrrolidone, and 3 parts by weight of acrylic acid. 35 Parts by weight of a fatty acid triglyceride (trade name "COCONARD RK", manufactured by Kao Corporation) as an organic liquid component and 0.26 part by weight of a cross-linking agent with respect to 64.74 parts by weight of the solid content of a pressure-sensitive adhesive containing the copolymer as an adherent polymer were added to the pressure-sensitive adhesive. The contents were stirred in an ethyl acetate solution to provide a composition for forming a pressure-sensitive adhesive layer.

A patch 12 was obtained in the same manner as in Example 3 except that the resultant composition for forming a pressure-sensitive adhesive layer was applied onto a release liner (polyester film whose surface had been subjected to release treatment) so that its thickness after drying became 60 μm, and the applied composition was dried to form a pressure-sensitive adhesive layer.

The failure modes of the patch 11 and the patch 12 were measured in the same manner as in the patches 1 to 10. As a result, none of the patches underwent anchoring failure. The foregoing shows that an anchoring force-improving effect is exhibited in other acrylic pressure-sensitive adhesives as well.

Example 13

(1) 20 Parts by weight of polyisobutylene (manufactured by BASF, viscosity-average molecular weight: 4,000,000), 20 parts by weight of polyisobutylene (manufactured by BASF, viscosity-average molecular weight: 55,000), and 60 parts by weight of polybutene (dynamic viscosity: 4,000 $mm^2/s$ (100° C.)) as a tackifier were mixed in toluene to provide a rubber-based pressure-sensitive adhesive.

(2) 10 Parts by weight of octyldodecanol and 7.5 parts by weight of polyvinylpyrrolidone (trade name "INF-10", manufactured by ISP) with respect to 82.5 parts by weight of the solid content of the rubber-based pressure-sensitive adhesive were added to the pressure-sensitive adhesive. The contents were stirred in a toluene solution to provide a composition for forming a pressure-sensitive adhesive layer.

(3) A patch 13 was obtained in the same manner as in Example 3 except that the composition for forming a pressure-sensitive adhesive layer obtained in the section (2) was applied onto a release liner (polyester film whose surface had been subjected to release treatment) so that its thickness after drying became 100 μm, and the applied composition was dried to form a pressure-sensitive adhesive layer.

Comparative Example 6

A patch C6 was obtained in the same manner as in Example 13 except that an undercoat agent was prepared without the addition of the silica particles.

The patches 13 and C6 were evaluated for their failure modes in the same manner as in the patches 1 to 10 and C1 to C5. As a result, the patch 13 did not undergo any anchoring failure but the patch C6 underwent anchoring failure. The foregoing shows that according to a support including an undercoat agent layer containing silica particles, an anchoring force-improving effect is exhibited in a pressure-sensitive adhesive layer containing polyisobutylene as well.

Example 14

95 Parts by weight of a commercial silicone-based pressure-sensitive adhesive (trade name "BIO-PSA 7-4202", manufactured by Dow Corning Corp.) and 5 parts by weight of silicone oil (trade name "Q7-9120", manufactured by Dow Corning Corp.) were mixed to provide a composition for forming a pressure-sensitive adhesive layer.

A patch 14 was obtained in the same manner as in Example 3 except that the resultant composition for forming a pressure-sensitive adhesive layer was applied onto a release liner (polyester film whose surface had been subjected to release treatment) so that its thickness after drying became 50 μm, and the applied composition was dried to form a pressure-sensitive adhesive layer.

Comparative Example 7

A patch C7 was obtained in the same manner as in Example 14 except that an undercoat agent was prepared without the addition of the silica particles.

An attempt was made to peel the release liner from each of the patches 14 and C7. As a result, the release liner was able to be peeled from the patch 14 because the pressure-sensitive adhesive layer of the patch 14 anchored to the support. On the other hand, the pressure-sensitive adhesive layer of the patch C7 did not anchor to the support and hence the layer peeled together with the release liner. The foregoing shows that according to a support including an undercoat agent layer containing silica particles, an anchoring force-improving effect is exhibited in a silicone-based pressure-sensitive adhesive as well.

Example 15

(1) 55 Parts by weight of 2-ethylhexyl acrylate, 5 parts by weight of N-hydroxyethylacrylamide, 40 parts by weight of N-vinyl-2-pyrrolidone, and 233.3 parts by weight of ethyl acetate as a solvent were-loaded into a reaction vessel provided with a cooling tube, a nitrogen gas-introducing tube, a temperature gauge, a dropping funnel, and a stirring machine, and were stirred at room temperature for 1 hour while nitrogen gas bubbling (100 mL/min) was performed. After that, the contents of the reaction vessel were heated, and when their temperature reached 60° C., 0.2 part by weight of 2,2'-azobisisobutyronitrile as a polymerization initiator was added. Such control that the temperature of the contents was kept at 60° C. was performed, followed by polymerization in a stream of a nitrogen gas for 6 hours. Next, the temperature was held at 76° C. for 15 hours. A solution of an acrylic copolymer (B) was obtained by the solution polymerization.

(2) 45 Parts by weight of isopropyl myristate as an organic liquid component with respect to 50 parts by weight of the solid content of the acrylic copolymer solution (B) were added to the copolymer solution. Further, 5 parts by weight of lidocaine were added as a drug to the solution. The contents were stirred in an ethyl acetate solution to provide a composition for forming a pressure-sensitive adhesive layer.

(3) A patch preparation 15 was obtained in the same manner as in Example 1 except that the composition for forming a pressure-sensitive adhesive layer obtained in the section (2) was applied onto a release liner (polyester film whose surface had been subjected to release treatment) so that its thickness after drying became 40 μm, and the applied composition was dried to form a pressure-sensitive adhesive layer.

Examples 16 to 23

Patch preparations 16 to 23 were obtained in the same manner as in Example 15 except that different kinds of silica particles were used. It should be noted that the pressure-sensitive adhesive layers of Examples 1 to 23 were substantially free of water.

Comparative Example 8

A patch preparation C8 was obtained in the same manner as in Example 15 except that a different kind of silica particles was used.

Comparative Example 9

A patch preparation C9 was obtained in the same manner as in Example 15 except that an undercoat agent was prepared without the addition of the silica particles.

The patch preparations 15 to 23, and C8 and C9 were each subjected to the following anchoring force test. Table 2 shows the results.

<Anchoring Force Test>

A patch preparation cut into a piece measuring 12 mm by 50 mm was used as a sample. The support surface of the sample was fixed to a SUS plate measuring 25 mm by 100 mm with a double-sided tape and its release liner was peeled. After that, a Celgard (manufactured by Hoechst AG) (release paper was attached to a surface different from the sample-attached surface with a double-sided tape) was attached to its pressure-sensitive adhesive layer surface with a roller having a load of 2,000 g. Next, the release paper was peeled under the conditions of a temperature of 23° C. and a humidity of 50% R.H. with a Tensilon tensile tester in a 180° direction at a rate of 100 mm/min. A load stress at the time of the peeling was measured.

TABLE 2

| | Silica | | | | Anchoring |
|---|---|---|---|---|---|
| | Average particle diameter (μm) | Pore volume (ml/g) | Shape | Trade name | force (N/24 mm, 180° Peel) |
| Example 15 | 6.0 | 1.2 | Amorphous | SYLOID 72FP*1 | >8 |
| Example 16 | 3.2 | 1.5 | Amorphous | SYLOID 244FP*1 | >8.4 |
| Example 17 | 3.9 | 1.6 | Amorphous | SYLYSIA 350*2 | >8.5 |
| Example 18 | 9.0 | 1.6 | Amorphous | SYLYSIA 380*2 | >8.7 |

TABLE 2-continued

| | Silica | | | | Anchoring |
|---|---|---|---|---|---|
| | Average particle diameter (μm) | Pore volume (ml/g) | Shape | Trade name | force (N/24 mm, 180° Peel) |
| Example 19 | 3.9 | 0.8 | Amorphous | SYLYSIA 550*2 | >8.1 |
| Example 20 | 4.5 | 1.5 | Spherical (sphericity: 0.9) | SYLOSPHERE C1504*2 | >8.7 |
| Example 21 | 4.0 | 0.4 | Amorphous | SYLYSIA 730*2 | 6.3 |
| Example 22 | 6.0 | 0.4 | Amorphous | SYLOID 63FP*1 | 5.9 |
| Example 23 | 11.3 | 0.4 | Amorphous | SYLYSIA 730*2 | 4.5 |
| Comparative Example 8 | 55.0 | 0.8 | Amorphous | COSMESILICA BQ60*2 | 3.1 |
| Comparative Example 9 | | | | | 3.8 |

*1Manufactured by W.R. Grace
*2Manufactured by FUJI SILYSIA CHEMICAL LTD.

As is apparent from Table 2, the patch preparations 15 to 23 each including an undercoat agent layer containing porous silica particles having a predetermined average particle diameter were improved in anchoring forces as compared to the patch preparations C8 and C9. The anchoring forces of the patch preparations 15 to 20 could not be accurately measured because the patch preparations each underwent cohesive failure. However, their actual anchoring forces are even larger than the measured values.

INDUSTRIAL APPLICABILITY

The patch or patch preparation of the present invention can be suitably utilized in, for example, the protection of a wound in a skin surface or the transdermal administration of a drug.

REFERENCE SIGNS LIST

100 patch
10 support
11 base material
12, 12' undercoat agent layer
20 adhesive layer

The invention claimed is:

1. A patch, comprising a support for a patch or patch preparation, the support comprising:

a base material containing an ethylene-vinyl alcohol copolymer resin film; and an undercoat agent layer laminated on the base material, wherein the undercoat agent layer contains a binder resin and porous inorganic particles having an average particle diameter of from 1 μm to 15 μm, and wherein the binder resin is a polyethylene terephthalate resin, an ethylene-vinyl alcohol copolymer resin, or a polyethylene resin; and a pressure-sensitive adhesive layer placed on one surface of the support to be adjacent to the undercoat agent layer.

2. A patch according to claim 1, wherein the porous inorganic particles have a pore volume of from 0.5 ml/g to 2.5 ml/g.

3. A patch according to claim 1, wherein the undercoat agent layer has a basis weight of from 0.1 g/m$^2$ to 10 g/m$^2$.

4. A patch according to claim 1, wherein the porous inorganic particles comprise porous silica particles.

5. A patch preparation, comprising the patch according to claim 1, wherein the pressure-sensitive adhesive layer further contains a drug.

* * * * *